United States Patent [19]
Place et al.

[11] Patent Number: 4,810,183
[45] Date of Patent: Mar. 7, 1989

[54] APPARATUS FOR CASTING THIN LAYER GEL MEDIA IN A MOLD AND SUBSEQUENTLY USING GEL FOR ELECTROPHORETIC SEPARATION WITHOUT REMOVING IT FROM THE MOLD

[75] Inventors: John F. Place, Geneva; André Bregnard, Le Lignon, both of Switzerland

[73] Assignee: IntraCel Corporation, Bridgetown, Barbados

[21] Appl. No.: 119,041

[22] Filed: Nov. 10, 1987

Related U.S. Application Data

[60] Division of Ser. No. 855,483, Apr. 24, 1986, abandoned, which is a continuation-in-part of Ser. No. 656,462, Oct. 1, 1984, Pat. No. 4,652,354.

[30] Foreign Application Priority Data

Oct. 4, 1983 [CH] Switzerland .................. 5390/83

[51] Int. Cl.⁴ .............................................. B28B 21/30
[52] U.S. Cl. ..................................... 425/434; 164/290; 164/302; 204/299 R; 264/311; 425/435
[58] Field of Search ............... 164/286, 290, 296, 302; 204/180.6, 182.7, 182.8, 299 R; 264/311; 425/425, 434, 435

[56] References Cited

U.S. PATENT DOCUMENTS

| 3,715,295 | 2/1973 | Tocci | 204/295 R |
|---|---|---|---|
| 3,927,826 | 12/1975 | Anderson et al. | 204/182.8 |
| 4,035,377 | 7/1977 | DeTroy | 204/299 R |
| 4,063,863 | 12/1977 | Hilmoe | 425/425 |
| 4,082,586 | 4/1978 | Osment | 264/311 |
| 4,169,036 | 9/1979 | Anderson et al. | 204/299 R |
| 4,325,897 | 4/1982 | Zerle et al. | 425/140 X |
| 4,338,071 | 7/1982 | Daubenbuchel et al. | 425/147 X |
| 4,350,481 | 9/1982 | Corea et al. | 425/425 |
| 4,362,685 | 12/1982 | Simoni | 264/311 X |
| 4,416,841 | 11/1983 | Corea et al. | 264/311 X |
| 4,422,984 | 12/1983 | Neefe | 264/311 X |
| 4,431,506 | 2/1984 | Gorman, Jr. et al. | 204/299 R |
| 4,440,699 | 4/1984 | Smid et al. | 425/140 X |
| 4,478,567 | 10/1984 | Schaer | 425/425 |
| 4,517,145 | 5/1985 | Knopf | 425/140 X |
| 4,533,307 | 8/1985 | Ansorge | 204/299 R X |
| 4,534,916 | 8/1985 | Wichterle | 264/311 X |
| 4,657,655 | 4/1987 | Smoot et al. | 204/299 R |

Primary Examiner—Jay H. Woo
Assistant Examiner—C. Scott Bushey
Attorney, Agent, or Firm—Cushman, Darby & Cushman

[57] ABSTRACT

A mold for the casting of thin, cross-linked, polymerized resin films is subjected, when being filled with the liquid to be polymerized, to a centrifugal force field exceeding that of the earth gravitation field, the whole being for equalizing the intimate structure of the polymer and to expel therefrom the bubbles of gas possibly present therein. After curing the gel, a mixture of compounds to be separated by the application of an electric field is introduced into the gel and the latter is subjected to electrophoresis within the mold itself.

6 Claims, 3 Drawing Sheets

APPARATUS FOR CASTING THIN LAYER GEL MEDIA IN A MOLD AND SUBSEQUENTLY USING GEL FOR ELECTROPHORETIC SEPARATION WITHOUT REMOVING IT FROM THE MOULD

This application is a divisional application of Ser. No. 855,483, filed Apr. 24, 1986 and now abandoned, which is a continuation-in-part of Ser. No. 656, 462 filed Oct. 1, 1984, now U.S. Pat. No. 4,652,354.

The present invention concerns a method for performing thin layer electrophoretic separation in a thin layer medium cast in a flat transparent mould; the separation is carried out within the casting cavity of the mould, i.e. without separating the gelled medium from the mould or in some cases without even opening the mould. The invention also applies, without saying specifically hereafter, to other separation techniques related to electrophoresis, namely isolelectric focusing, chromatography, thin layer chromatography and others.

It is known that the techniques of electrophoresis called also sometimes electrochromatography consist of subjecting to an electric field provided by two electrodes, one anode and one cathode, an electroconductive solution of positively or negatively ionized molecules so as to cause the migration of the latter in direction of the electrode having a sign opposite to that of the charge of said molecules. The rate of electromigration of the charged molecules is determined by some of their physical chemical parameters, namely their mass, their charge, and the diffusion constant in the medium under consideration which enables to effect the separation of the various chemical species as a function of parametric values specific to these various species. One therefore obtains, at the end of the operation, a chromatogram or electropherogram wherein, after development, the various species of molecules thus separated appear under the form of points or spots or successive areas more or less diffuse depending of the efficacy of the separation.

This efficiency of the separating capacity is related among others to the temperature of the electrophoretic medium because the higher the temperature, the greater the effects of thermal convection, as well as the random movement of the molecules (diffusion) and the less sharp the electrophoregram. Besides, it is evident that such defects increase in proportion to the duration of the electrophoresis, the time necessary to effect, an effective separation of the species to be identified being naturally a function of their relative displacement rates in the electric field. Therefore, in order to minimize as much as possible the aforementioned shortcomings and also for evident practical reasons, it is necessary that the duration of the electrophoresis be as short as possible while being long enough to ensure that the various species to be identified are sufficiently separated from each other to be distinguished. It will therefore be advantageous to increase as much as possible the migration velocity of the components under analysis but preferably without raising the temperature.

Now, a charged particle (q) which moves in an electroconductive liquid under the influence of an electric field of magnitude H displaces itself at a rate v determined by the existence of two oppositely acting forces of equal value: a first force $qH$ acting in the direction of the displacement and a second force $KTv/D$ due to the friction of the particle on the medium and thus acting in an opposite direction (K is the Boltzmann constant; T is the absolute temperature and D is the diffusion constant, a parameter specific to the molecule under discussion). Thus, if T is maintained constant, it is possible to increase v by increasing H. Now, in such a medium, H is defined by the following relation $H = i\gamma A$ where i is the intensity of the current in the electrolysis medium, $\gamma$ is the conductance and A is the cross-section of the electrophoretic medium. As a consequence, for increasing H without increasing T (that is to say without increasing the energy dissipation by an increase of the current i), one will have to act by decreasing the thickness of the electrophoretic medium.

Under usual practice for separating organic molecules such as proteins or nucleic acids, it is possible to use electrophoretic media consisting of gels (agarose, starch, polyacrylamide, etc..) more or less cross-linked according to the needs. Such gels have the property of decreasing the convection displacements in the electrophoretic liquid and to improve the fractionation of the molecules to be separated as a function of their size and their bulk relative to the mesh size of the network constituted by the gel as well as with regard to their surface affinity properties relative to the molecules of the latter.

For the above reasons, attempts have recently been made to prepare electrophoretic gels in the form of films as thin as possible (of the order of 20 to 500 $\mu$m), the use of such thin films presenting the following advantages: a decrease in the heating due to the Joule effect with the possibility of applying larger electric fields allowing for a better separation within shorter analytical periods. Better dissipation of the heat produced with, as a consequence, a smaller temperature gradient through the gel thickness and a decrease of the effects which depend on the thermal convection movements in the medium. Also, improved sensitivity is obtained by reason of the reduction of the total amount of sample required for the analysis.

Many publications have issued recently in this field among which one can cite the following: W. ANSORGE et al, J. Chromatography 202 (1980), 45–53; P.G. RIGHETTI, Electrophoresis '81(1981), De GRUYTER & CO, Berlin-New York, p. 2–16 et 182–188; J. W. JORGENSON et al, Clin. Chem. 27 (1981) 1551–1553; H.R. MAURER et al, Analyt. Biochem 46 (1972), 19–32; V. ANSELSTETTER, J. Chromatography 172 (1979), 49–56; C.J. Van OSS, Methods Immunodiagnosis (1973), 175–194; A. GOERG et al, Analyt. Biochem 89 (1978), 60–70; A. GOERG et al, J. Biochemical and Biophysical Methods 3 (1980), 273–84.

According to the aforementioned references, the techniques used for preparing thin layer gels comprise the following embodiments (1) Constructing a mould by means of two rigid plates (made of glass for instance) fitted to each other by cross-bars (one base cross-bar and two side cross-bars) and filling this mould placed vertically by introducing therein, by means of a filling device, the solution of monomers whose subsequent polymerization provides the gel sought after;

(2) A different technique involves applying the monomer solution over a plate provided with cross-bars on three of its sides and held horizontally, then applying a second plate on the first one in the manner of closing a book, both plates being maintained ultimately in a parallel orientation to each other by the cross-bars so as to eliminate the excess of the liquid caught in-between, this excess being driven off and escaping through the opening which results on one side of the mould, from the absence of a fourth cross-bar.

(3) According to a technique resembling the previous one after depositing the solution on a first plate, one progressively slides the second plate over the first one so as to push off, in the direction of the opening of the mould by a scraping effect, the excess liquid.

All these methods require great operating skill to avoid the entrapping of small air bubbles in the liquid between the plates. Especially if the thickness of the mould is less than 1 mm, it is practically impossible to completely eliminate the possible imperfections due to the air bubbles. For thin layer gels, the techniques (1), (2) and (3) mentioned above, are thus lengthy, costly to be implemented and require great operating skill.

Besides, the defects of homogeneity of the thin layer gels can amplify some drawbacks in connection with the bringing about of the electrophoresis operation such as losses of water in the gel, some preferential displacement of the samples to be analyzed in the surface portions of the gel and thermal convection effects in imperfectly cross-linked areas of the medium.

In addition, some current electrophoretic practice requires removing the gelled electrophoretic medium from the mould or removing one plate of the mould before carrying out the desired electrophoretic separation. The shortcomings here are risks of mechanically damaging the gel, risks of contamination by outside pollutants or contact with air.

Summarizing briefly, the process of the invention is for moulding gels into films for thin layer electrophoresis and other related techniques of separation by using a mould for thin films in which the principal wall surfaces are transparent and, at least in part, separated one from the other by a distance corresponding to the thickness of the film to be formed and subsequently applying thereto said techniques to separate into components a sample mixture of said components. This process comprises the steps of:

(a) filling the mould with a gellable mixture to be cast by gravity and subjecting it to a centrifugal gravity field exceeding 3 g for effecting efficient debubbling and homogenizing thereof:

(b) curing said mixture into a gel;

(c) introducing into the mould in contact with said gel a sample mixture to be subjected to separation;

(d) electrically connecting the end portions of the gel within the mould to the terminals of a power source suitable for electrophoresis; and (e) carrying out said electrophoresis operation for a time sufficient for separating the sample mixture into its components.

For implementing this process, one uses a mould formed by two rigid plates maintained substantially parallel one to the other at a distance of about 5 to 500 $\mu$m, for instance by means of cross-bars as in the previous art. The opening of the mould located at an edge of the mould or at close proximity thereto, is arranged in a manner such that when a liquid is introduced therein, the latter flows along the inside surface of the parallel faces, this being like in the case of the prior art moulds which are placed, when being filled, in a vertical position.

In order to prepare the gel according to the process of the invention, the mould is filled with a liquid composition or an electroconductive solution of one or more substances, for instance monomers or prepolymers susceptible to set or to harden into a mass and thus to provide a gel. One allows the gas or air bubbles or other local inhomogeneities possibly present in the liquid of the mould to be eliminated during the centrifugation, then, when the fluid becomes homogeneous, one causes or allows it to harden by the usual means; catalytic polymerization or otherwise, or cooling in the case when a hot gelatin solution is involved, so as to obtain a gel. The particular feature which characterizes this process relatively to the prior art is the fact that one operates under the influence of an artificial gravitational field, this field being caused by the rotation of the mould and the forces therefore provided being directed so that the filling liquid is driven from the mouth of the mould towards the bottom of this mould. Therefore, this gravitational field is applied to the mould exactly like the terrestrial field in the case of a mould to be filled vertically, the difference provided by the invention being, in connection with the intensity of this field due to the rotation of the mould. This intensity of the field can attain several g, for instance 5 to 200 g's, or more if desired.

The use of a gravitational field of intensity over that of the terrestrial field for filling moulds intended for moulding thin films for electrophoresis presents the main advantage of a very fast and complete elimination of air bubbles and local inhomogeneity defects which are possibly present in the liquid to be polymerized. This effect, per se, is not new because it is known to degas liquids by centrifugation (see for instance, Chem. Ing. Tech 44 (1972), 497–503 49 (1977), 747; Japanese patent application Kokai 80 135,618); however, it does not seem that such a technique has ever been proposed for the moulding of thin layer gels for electrophoresis applications or for other related techniques (thin layer chromatography, isoelectric focusing, etc..). Other references in the field are U.S. Pat. Nos. 4,534,916 (Wichterle), 4,533,307 (Ansorge), 4,517,145 (Knopf), 4,440,699 (Smid et al), 4,431,506 (Gorman Jr. et al), 4,422,984 (Neefe), 4,416,841 (Corea et al), 4,362,685 (Simioni), 4,338,071 (Daubenbuchel et al), 4,325,897 (Zerle et al), 4,169,036 (Anderson et al).

Another advantage of moulding such gels under the influence of a centrifugal force is to enable in some cases to achieve a property gradient after polymerization. Indeed, under the influence of a force that varies radially in proportion to the distance from the center to the periphery ($F_c = V^2/r = \omega^2 r$), a solution of monomer not yet polymerized or being polymerized subjected to a rotation effect can, if the angular velocity is sufficient, densify at the periphery and rarify at the center. If a polymerization is completed during rotation the variable density gradient will be maintained in the terminated gel; such a technique enables thus obtaining thin layer gels with variable properties according to a given function, this being with solutions which are normally homogeneous at the start. It will be noted in this connection that for obtaining property gradient gels according to usual techniques, one proceeds by simultaneously introducing into the mould two monomer solutions with different concentrations, the ratio of the addition rate for the two components being varied in the course of time according to a given relationship. The process of the invention enables to obtain gradient gels in a much simpler and better controlled manner. The invention is also suitable for the preparation of composite gels by the successive additions of solutions of different natures or concentrations, as sequentially polymerized gels.

The gels which can be prepared according to the invention are of various natures and comprise practically all cross-linked polymers generally usable in this field. Among the latter, one can cite the gels of gelatin, agarose, starch, polyacrylamide and others. In the case of gelatin solution, the latter is cast under heat and the hardening takes place afterwards by cooling. Regarding the polymerization of monomers, this can be effected according to usual means, for instance by incorporation into the solution before moulding of initiators or activators of polymerization normally required for polymerization at the considered temperature, the mould being maintained or not under rotation until the end of polymerization. Examples of these types of gels and the means for polymerizing them are found in the above-mentioned references. Although as has been shown above, it can be interesting to proceed with the polymerization under the influence of a centrifugal force, this is not necessary in the cases when the centrifugation is only intended to improve the intrinsic quality of the gel material (homogeneous gels without air bubbles); in such a case, it is possible, after the debubbling step, to stop the rotation of the mould and allow the polymerization to proceed under rest.

In contrast, the polymerization of a solution or mixture of photopolymerizable monomers can be effected by incorporating to the mixture one or several appropriate photoinitiators. Once the mould is filled and the solution is debubbled by centrifugation, the latter is hardened by irradiation by means of a convenient actinic source, this operation being carried out as well on standing as under rotation. In the latter case, each zone of the mould regularly passes, in turn, in close facing relation with the irradiation source with the result that the exposure of the solution to be polymerized is particularly regular and the gel which results therefrom is very homogeneous.

One of the significant novel features of the invention is to perform the subsequent separation operation within the mould itself without removing first the separation medium therefrom or opening the mould. Moulds for accomplishing this objective are possibly made of formed transparent plastic such as polyacrylate, polystyrene, polycarbonate, polyethylene, polypropylene, polyester, polyamide or copolymers thereof; such moulds are disposable and are generally thrown away after use unless stored for docketing. The moulds are provided with openings giving access to some portions of the gel required for introducing the samples to be subjected to separation. The openings are normally plugged during filling with removable plugs. Otherwise the sample can also be added by the mouth of the mould either separately or in admixture with some gellable liquid portion. Such liquid portions can be used as stacking gel portions.

For establishing electrical connection at both ends of the gel medium when performing an electrophoretic separation within the mould, the bottom portion thereof can be made available either through an open end in the mould or by removing the end wall thereof (for instance removing the terminal cross-bar). The end of the mould is normally closed during filling with the gellable solution either by a plug or by the effect of the centrifugal force holding the mould in pressing relationship against some gasketed peripheral retaining element of the rotating device.

When the gel has set in the mould, the liquid retaining closing elements can be withdrawn to make the ends of the gel free. The mould can then be placed under conditions whereby each end of the gel is in electrical contact with one terminal of a DC power source; for instance the mould can be placed in a container provided with electrolytes at a potential difference, i.e. the mouth of the mould is in contact with a (+) electrolyte and the bottom of the mould is in contact with a counterpart (−) electrolyte. Otherwise, flat metal electrodes can be run into each mould open end. More details will be provided hereafter.

Conditions under which electrophoretic (or related) separation occurs is no part of the present invention. Such conditions are purely standard and the electrical and other operating parameters are known to those skilled in the art.

Another novel feature of this invention is the reading of the electropherogram. For instance, in one embodiment described hereafter, the mould is dismantled at the end of the separation operation and the gel is stained as usual for observation of the separated spots. In a more sophisticated embodiment also described below, the mould is not taken apart but simply removed from the electrophoresis apparatus and subjected to scanning in a spectrophotometer. By properly calibrating the scanner holder, the position of the spots at maximal absorption can be recorded either on the plate itself or on a recorder connected to the scanner. The spectrophotometer can operate at any suitable wavelength at which energy absorption by the separated substances will occur. Usually, for protein separation, the UV range is preferred. However a mixture of proteins can also be prestained with a stain such as Remazol Brilliant Blue (see Clinical Chemistry 29 Nr.1 (1983), 42–44) or prelabelled with a fluorescent signal generator such as FLUORESCAMINE ® which can thereafter be measured at the relevant wavelength with appropriate equipment. Of course the material of the mould (plastic, glass, quartz or other) must be selected to be reasonably transparent in the ranges selected for analysis.

For the description that follows, reference is made to the annexed drawing that represents two devices for embodying the invention and one variant.

Figure 1:
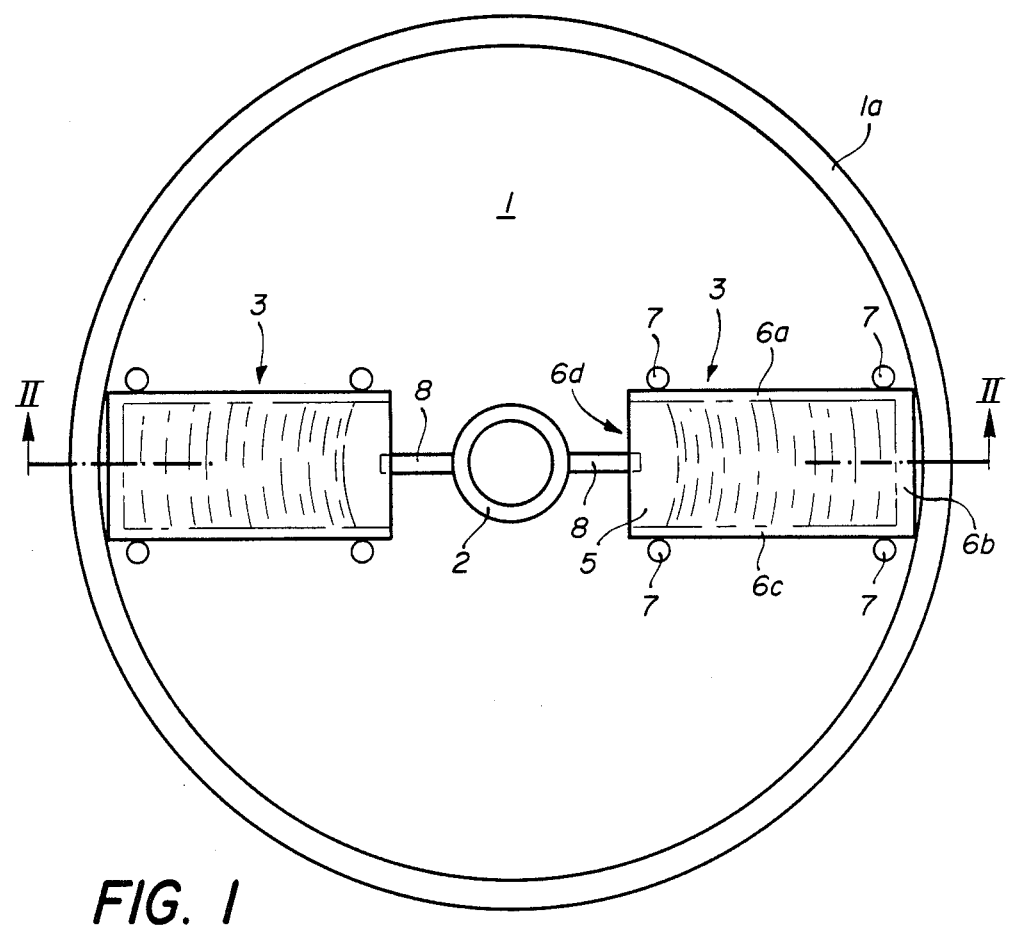
FIG. 1 represents in plan view the essential parts of a device allowing the introduction of a solution into a mould and its debubbling by centrifugation.

The device represented in FIG. 1 comprises the main following elements: a circular plate 1 mounted on a hollow shaft 2, this plate being used to support one or several moulds 3 intended for moulding thin polymer films in the form of gels. Each of the moulds 3 comports a lower rigid plate 4 and an upper rigid plate 5 (made of glass or of plastic) these plates being maintained approximately parallel by assembly means constituted by cross-bars 6a, 6b and 6c. The moulds 3 are maintained on the plate on one hand by a shoulder 1a of the latter and on the other hand by detachable studs 7 made of plastic whose removal enables to withdraw the moulds after their filling with a liquid and possible subsequent polymerization of this liquid. The hollow part of the shaft 2 communicates with the entrance 6d of the moulds by a flexible duct 8 whose external end is flush with opening 6d or penetrates very slightly therein.

Plate 1 is mounted on a frame not represented and rotated by a motor also not represented.

Figure 2:
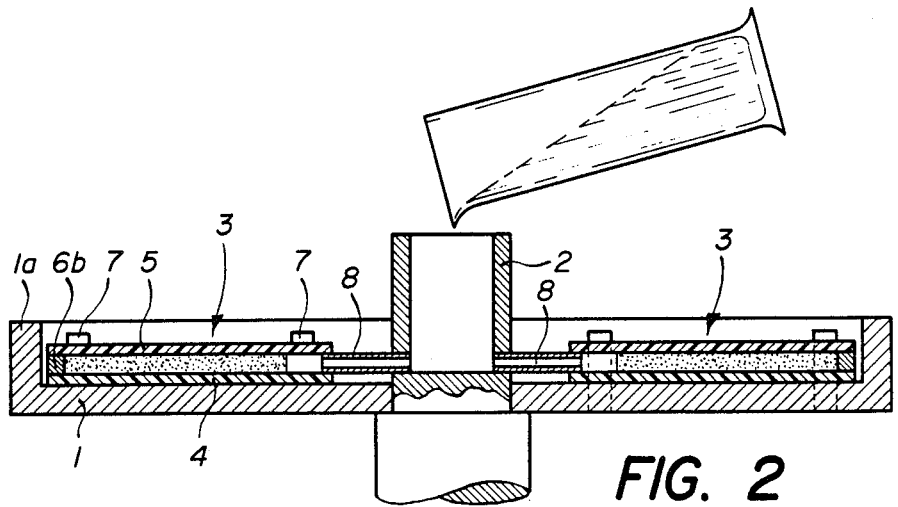
FIG. 2 represents a cross-section of said device along the line II—II of FIG. 1.

For filling one or several moulds, this mould or these moulds are mounted on the plate and maintained firmly horizontally by means of studs 7. Naturally, the plate can be made to freely rotate and can be balanced either by the presence of a second mould (as shown in the drawing) of by an appropriate counterweight. After checking that the output ends of duct 8 are well in communication with the opening 6d of the mould, the assembly is rotated and the solution intended to provide the gel is introduced into the hollow upper part of the axis 2 as schematically shown in FIG. 2. The liquid penetrates by means of tube 8 into the mould 3 and, under the action of the centrifugal force, it accumulates to the bottom of the latter while the air bubbles and other defects possibly present in the liquid are rapidly expelled by reason of the existence of the gravitation field markedly exceeding that of gravity. Naturally, the rate of rotation of the rotatable assembly depends on the working conditions, the nature of the solution, the viscosity, the flow parameters and others and will be determined by the specialist as a function of these factors and of the operating means. The solution to be polymerized (for instance an aqueous 5% solution of acrylamide containing as cross-linking agent, for instance 1-2% of methylen-bis-acrylamide) can contain either a radical polymerization initiator, for instance a peroxide, or a photoinitiator (for instance riboflavin or any other appropriate photoinitiator). In the first case, once the mould is filled, it is maintained under rotation (for instance at reduced speed) the time required for the liquid to harden into a mass and become unable to escape through the mould opening when the movement of the latter is stopped. In the second case, an actinic source is placed above the device under rotation (for instance a mercury vapor lamp providing 40 w/dm$^2$ at 15 cm) and one proceeds to the irradiation of the moving mould, this irradiation being from a few seconds to a few minutes depending on the liquid composition. It is noted that depending on the kind of liquid used and the mould dimensions, the liquid may remain in the mould even without rotation.

Once the liquid is polymerized, the rotating device is stopped and the film of gel is used in an analytical operation or in a preparative electrophoretic separation as heretofore mentioned.

Figure 3:
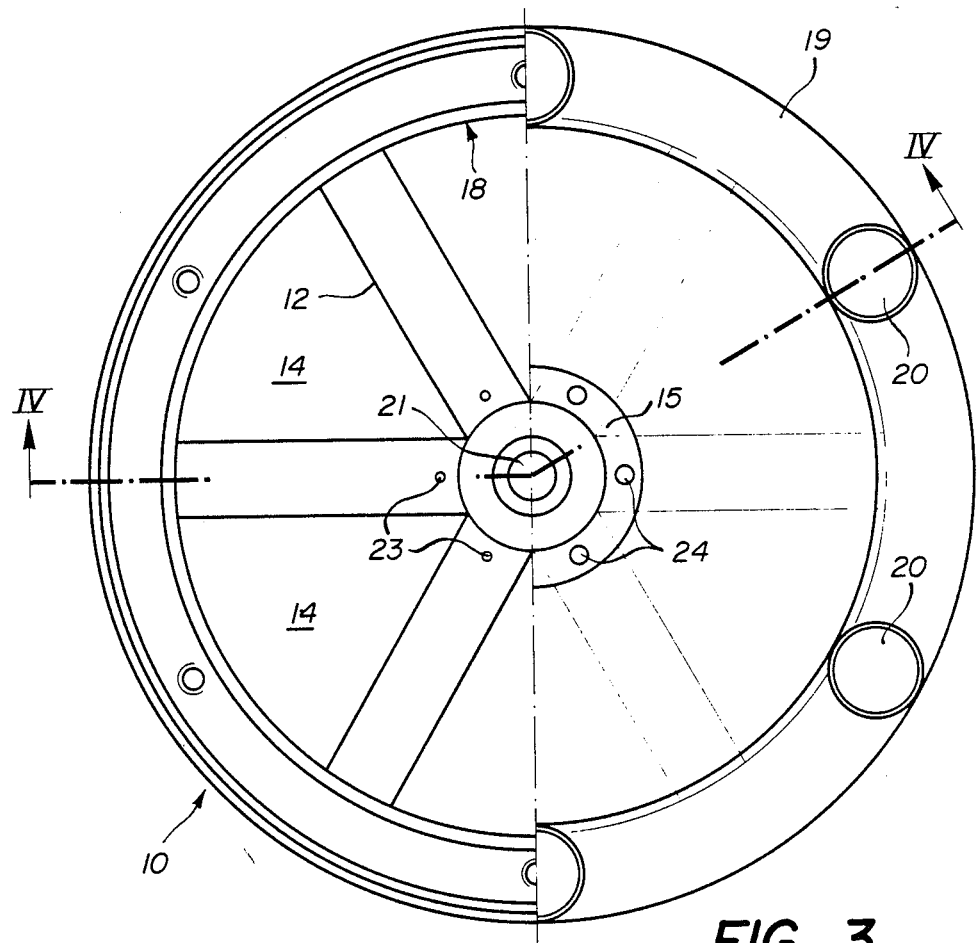
FIG. 3 is a plan representation with partial sections of a mould.
Figure 4:
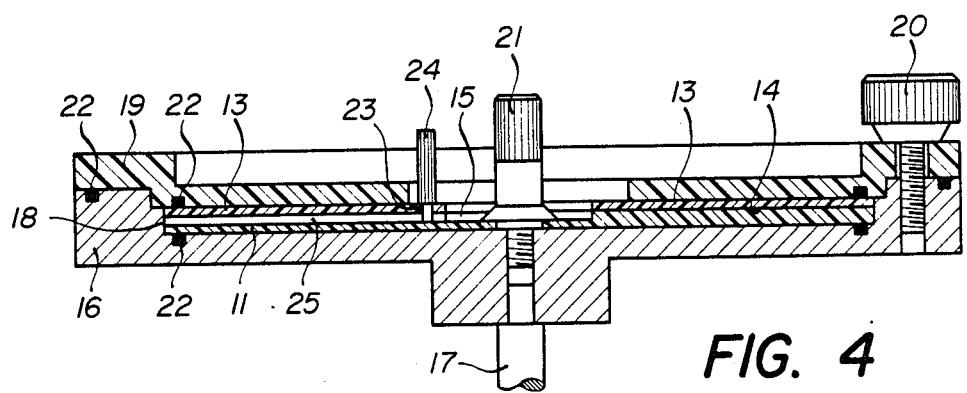
FIG. 4 represents a vertical section of the device of FIG. 3 along the line IV—IV of FIG. 3.

The device represented on FIGS. 3 and 4 comprises a mould 10 constituted by a lower disc 11, pierced at its center, in which are machined radial recesses 12, and a second disc 13 also pierced at the center adjusted concentrically on the upper face of disc 11. Recesses 12 constitute the inside volume of the mould which comprises as shown on the drawing, six independent compartments 12. These compartments are delineated on one hand by the bottom of recesses 12 and the portions of the disc 13 which cover these recesses, these surfaces constituting the main faces of the mould, and on the other hand, by the side-walls of sectors 14 of the disc 11 (sectors which constitute the means for assembling and maintaining in an abutting position the main faces of the mould) whose level with regard to the bottom of recesses 12 determines the thickness of the inside volume of the mould and consequently that of the desired films of gel. The edges of these sectors 14 constitute, in the case of each compartment, two of the secondary faces of the mould.

The diameter of the central hole of disc 13 is smaller than that of the corresponding hole of disc 11 so as to provide, by interrupting the abutting and assembling means of the main faces, annular opening 15 for filling the various compartments of the mould.

The present device further comprises a lower circular plate 16 mounted on a rotation axis 17 and comporting a shoulder 18 whose height approximately corresponds to the thickness of the mould, the latter being fitted into the recess comprised between the bottom of plate 16 and said shoulder 18; the edge of the latter constitutes then the third lesser face which limits the volume of the mould 10.

The present device further comprises a circular lid 19 which can be affixed to plate 16 by knurled knobs 20 and a central bolt 21 enabling to make integral together the mould 10 and the plate 16. The tightness to liquids of the various organs thus put together is ensured by a series of O-ring joints 22. Finally, the device further comprises, pierced in a circular central zone of disc 13, holes 23 the cross-section of which can take any shape (circular, square, rectangular slit-like or others) in which one can engage elements in form of removable pegs 24 whose lower part, which presents a section corresponding naturally to the inside dimension of holes 23, rests against the inside face of the disc 11. The purpose will be seen later of these elements 24 whose shape and cross-section can be any provided their lower part matches with the shape of holes 23, that they can be easily introduced therein and that they can be extracted manually therefrom.

In order to implement the process of the invention by means of the present device, one preferably proceeds as follows: at the beginning of the operation, the main elements, mould, plate and lid are taken apart and the discs 11 and 13 (generally made of glass or of a plastic transparent to actinic rays) are carefully washed, rinsed with distilled water and dried. These various parts are thereafter reassembled and the assembling elements correctly tightened and locked by means of bolt 21 and knobs 20. The pegs 24 are thereafter introduced in the respective holes 23 and the device is rotated by means of a motor not represented. When the desired angular velocity is reached and the centrifugal force field is achieved, a solution is introduced, for instance by means of a syringe whose tip is directed through the opening 15, the polymerization of the solution will provide a gel. The addition is continued until the level of the liquid (indicated by FIG. 25) is flush with the annular edge of disc 13 (or at least when it passes the position of holes 23). After a waiting period provided to allow for debubbling and homogeneizing, one then proceeds to the polymerization of the liquid as indicated with regard to the first embodiment, the lid 19 being made of a transparent plastic, for instance a "LUCITE UV", and when the liquid has solidified into a gel, the pegs 24 are withdrawn, the removal of the latter providing, in the mass of gel, holes or recesses usable subsequently for the introduction into the gel of the samples to be subjected to electrophoresis. It can be thus easily understood that these recesses can be of any shape according to the needs, the sample size and the shape of the electropherogram which one desires to obtain. Thus these recesses can have a square, circular or elongated shape, for instance an arc of a circle extending the full width of compartment 12. As a variation, several holes or wells side by side are possible by providing a number of holes 23 and elements 24 per compartment exceeding 1.

It should be remarked that the present embodiment enables to easily achieve gels with two or several superimposed sections by adding in succession, when filling the mould, two or more solutions. In particular, a technique is commonly used in which is provided near the center of the rotation a thin portion of a particular gel (stacking gel) which enables an appropriate preliminary grouping of the components of the sample to be analyzed before the latter can penetrate in the main portion of the gel film. Thus, for instance, the stacking gel has the property to allow a sample, having first been added at only one point to spread over the entire width of compartment 12. To achieve such a gel film, one successively uses two filling solutions; the first one accumulates from the periphery of the mould to the $\frac{2}{3}$, for instance, of the total capacity thereof and the second one provides a central annular portion in the remaining $\frac{1}{3}$ of the mould volume. It should be remarked that, according to one particular technique, one can add, as the next filling portion, a solution (also hardenable subsequently when the gel is formed) containing precisely, in addition, the sample to be subjected to electrophoresis. The advantage of this modification resides in providing a perfectly regular distribution of the sample over the main body of the gel in which the electrophoresis is to be carried out.

Figure 6:
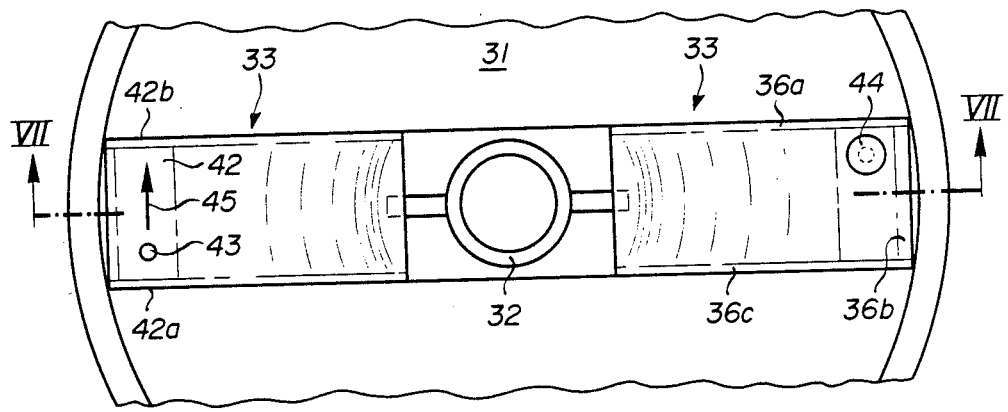
FIGS. 6 and 7 illustrate a variant of the embodiment of FIGS. 1 and 2.
Figure 7:
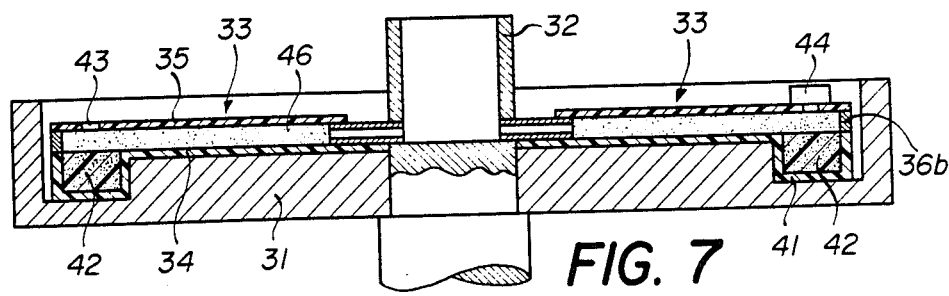

The variant represented in FIGS. 6 and 7 comprises generally the same elements as the device illustrated on FIGS. 1 and 2, namely the plate 31, a hollow shaft 32 and moulds 33. These moulds are constituted by a lower plate 34 and an upper plate 35 assembled by cross-bars 36a, 36b, and 36c. The lower plate 34 is not flat on the whole surface thereof like in the device of FIGS. 1 and 2 but shows in the vicinity of the periphery a U-shaped configuration 41 so as to provide at the bottom of the mould a recess or groove 42, the depth of this groove being of the same order of magnitude as, or deeper than, the thickness of the mould such as illustrated on the drawing by the distance between plates 33 and 34. Further to the aforementioned elements, the present variant also comprises means identical to that already disclosed with regard to the embodiment of FIGS. 1 and 2, namely lateral tubes 8 for filling the mould and locking elements not represented. Besides, the upper plate 33 comprises openings 43 which can be plugged with plugs 44.

For casting a film according to the invention by means of the above-mentioned modification, one proceeds identically as previously disclosed with however the following additional phases: first the upper plate 31 and the lower plate 34 are assembled with the cross-bars 36a, 36b, and 36c, the part designated by 41 fitting into an appropriate groove of the plate 31. Then the groove 42 is filled by usual means with a first composition providing a first gel whose quantity is such that its upper level is flush with the inside surface of the main part of plate 34. Thereafter the first composition is cured, the upper plate 35 is put into place and a sample to be analysed by electrophoresis is injected through opening 43 so that it comes into contact with the first gel in the vicinity of one of its ends 42a as indicated on the drawing. Once the sample has been incorporated into the first gel, the mould is withdrawn from the hollow plate 31 and after having contacted the ends 42a and 42b of the gel with electrodes suited for performing an electrophoresis analysis according to usual means, this electrophoresis operation is carried out for a time sufficient to separate the sample into its various components, the latter migrating sidewise relative to the mould as indicated by the arrow 45. Once this first electrophoretic separation is completed, the removed components are reassembled on plate 31 and the forming of a second gel in area 46 is carried out exactly as in the embodiment illustrated previously with reference to FIGS. 1 and 2. Once this second gel has hardened, it is electrolytically in contact with the first gel and it is therefore possible by subjecting this second gel to a new electrophoresis operation according to usual means but oriented at right angle relative to the arrow 45 to provide a new separation in a longitudinal direction of each of the components which were individualized in the first electrophoresis. Such operation is performed after removing the mould from the rotatable device and inserting electrodes into the gel at both ends of the mould, i.e. through its mouth and through its bottom after removing cross-bar 36b. This embodiment enables therefore to prepare by very simple means a thin layer gel for electrophoresis in which the sample is distributed in fractionated form over the whole width of the electrophoresis area, this fractionation resulting from a first electrophoretic operation directed at right angle (or according to any angle preferably near 90°) relatively to that of said electrophoresis.

The following examples illustrate the invention

EXAMPLE 1

(for illustrating super-g gravity in gel casting)

A device such as that represented on FIGS. 3 and 4 was used which presented the following significant parameters: diameter of the mould 20 cm; thickness 0,1 mm; rotation velocity variable between zero and 3000 r.p.m.; filling liquid: acrylamide solution at 5% with a density about 1.

Before undertaking a practical test of debubbling according to the process of the invention, the radial centripetal ascending force was calculated to which the air bubbles enclosed in the filling liquid in the mould are subjected as a function of their distance from the rotation center and their depth of immersion in the liquid. It will be understood that the term of ascending force is used to designate the force to which the bubbles are subjected by virtue of the corresponding volume of displaced liquid, although this force is directed actually horizontally. For this calculation, the following basic elements have been used for the understanding of which reference is made to FIG. 5: on the graph of FIG. 5 have been indicated in cm, on one hand on the X axis the distance (x) from the rotation axis at which the air bubble trapped in a rotating liquid is located as well as the depth (h) at which it is placed relative to the upper level of this liquid whose total depth is 7 cm, and on the other hand, (Y axis) the centripetal force opposing the gravitation field to which it is subjected. These values have been indicated for rotation velocities of 300, 600, 900 and 1200 r.p.m. respectively.

The other data of the calculation are the following:

| | |
|---|---|
| T (absolute temperature) = | 300° K. |
| n (number of moles of gas) = | $10^{-6}$ |
| R (gas constant) = | 8.317 kgm$^2$/sec.$^2$ · mol. °K. |
| At (external pressure) = | 100130 kg/m · sec.$^2$ |
| ρ (density of the liquid) = | 1000 kg/m$^3$ |
| h (height of the liquid) = | 0; 0.03; 0.07 m |
| x (rotation radius) = | 0.03, 0.06, 0.1 m |
| $a_c$ (centripetal accelaration) = | $\omega^2 \times$ m/sec$^2$ |
| ω (rotation velocity) = | 2 ω/t radians/sec |
| t (time of one revolution) = | 60 × (rpm)$^{-1}$ sec |
| M (average molecular mass of air) = | 28.56 i.e. 0.02856 kg/mole |

In the following table, the following data are indicated as a function of the rotation frequency (rpm) and of the distance from the center (x), the ascending forces in Newtons×10$^{-6}$ and, within parenthesis, the centripetal acceleration (in multiples of g, the acceleration of gravity) to which the bubbles placed at such distances are subjected, these last values being obtained from the following relation (2π.rpm/60)$^2$.x /9.81.

| | Ascending force and (acceleration) for x expressed in m | | |
|---|---|---|---|
| rpm | x = 0.03 | x = 0.06 | x = 0.1 |
| 300 | 737 (3) | 1448 (6) | 2298 (10) |
| 600 | 2947 (12) | 5506 (21) | 7696 (40.2) |
| 900 | — (27.2) | — (54.3) | — (90.5) |
| 1200 | 11790 (48.3) | 18360 (96.6) | 18860 (160) |

Figure 5:
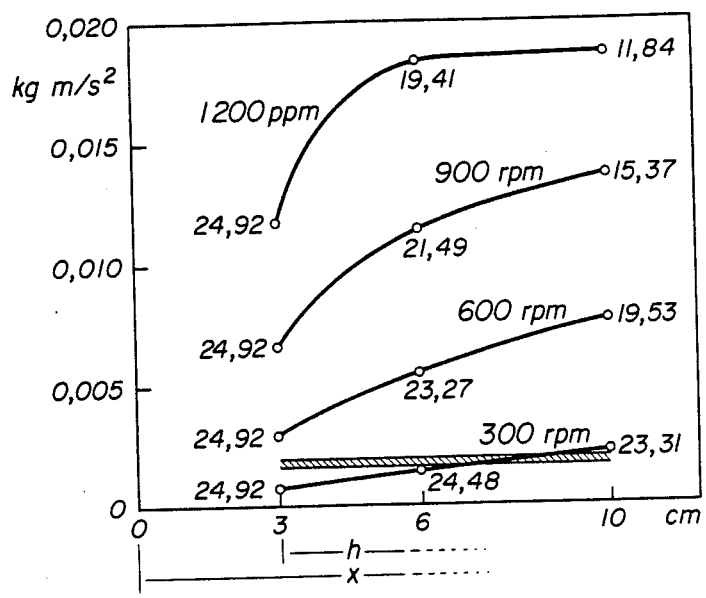
FIG. 5 is a graph for illustrating the relation which exists between the position of a gas bubble immersed at various depths in a liquid subjected to a centrifugal force and the escaping force to which this bubble is subjected.

The ascending forces indicated in FIG. 5 are calculated by taking account of the volume of the bubble immersed in the liquid under rotation and of the hydrostatic force which it generates by reason of the corresponding volume of liquid displaced minus the centrifugal force. The following relation is used:

$$\text{Ascending force } (N) = \left( \frac{n \cdot RT}{At + \rho \cdot h \cdot a_c} \right) \cdot \rho \cdot a_c - n \cdot M \cdot a_c$$

In FIG. 5, the four groups of three values of the aforementioned ascending forces (as a function of the rotation frequency) were plotted vertically on the Y axis calibrated in N (or kg.m/sec) then these groups of points were approximately connected together to provide a curve showing the relative variation of these forces as a function of the rotation frequency and of the distance from the center. It can be seen on the graph that the resulting effect which is relatively progressive at low velocities is significant for higher velocities particularly near the rotation center and becomes less and less important when the distance therefrom increases. The reason for this behavior is evident because when the volume of the bubbles decreases under the influence of the compression, the contribution of the force due to the displaced liquid volume decreases relatively. The figures on the curves in FIG. 5 correspond to the calculated volume in μl of the bubbles at the pressure under consideration. The shaded horizontal area is intended to illustrate the film of the liquid subjected to centrifugation.

Regarding the experimental point of view, a 5% aqueous acrylamide solution was aerated by shaking with air (microbubbles were dispersed therein); then the solution was poured into the center of a rotating mould (see FIG. 2). This experiment provided the following observations: between 300 and 600 rpm, the removal of the bubbles from the samples was effected in about 3 to 2 min and very regularly, which was noted by observing under magnification at intervals the liquid subjected to centrifugation (the inspections were done after stopping the rotation). Under rotation velocities of 900 and 1200 rpm, the total removal of bubbles was achieved more rapidly but with the difference that a more pronounced effect was observed near the center for the first seconds of operation.

EXAMPLE 2

A circular mould such as that disclosed on FIGS. 3 and 4 and in conformity with the data of example 1 was used with the exception of the thickness between the plates, the latter being 50 μm. the following reagents were used:

Acrylamide (aqueous solution at 40%)

Methylene bis-acrylamide (ACRYLAMIDE-BIS) at 99.9% purity in aqueous solution (origin Bio-RAD). The product was purified by passing over the ion-exchange resin AG 501-X8 (BIO-RAD).

Solution TRIS (TRIZMA), pH of a 6.8 and 8.8 (adjusted with HCl). Sterilized in the autoclave.

Sodium dodecyl sulfate (SDS); solution at 20% in H$_2$O; purity 99% (Bio-RAD).

Ammonium persulfate; 10% aqueous solution freshly prepared.

Tetramethylethylenediamine (TEMED); origin BIO-RAD.

In a container adapted for a preliminary degassing under reduced pressure, there were mixed (for a 100 ml of solution) 25 ml of acrylamide solution and 0.33 g of BIS-ACRYLAMIDE. There were added thereafter 37.5 ml of TRIS 1M, pH 8.8 and 36.7 ml of distilled water. After degassing under reduced pressure, there were further added 500 μl of SDS (20%), 250 μl of persulfate (10%) and 75 μl of TEMED. After homogenization under agitation, this solution was poured by means of a pipette through the opening 15 of the mould under a rotation of 3000 rpm. The centrifugal force drove immediately the liquid to the periphery where it accumulated, the filling level (which is observed through the upper disc 13) moving progressively in the direction of the center. A few minutes after the end of the filling of the main portion (the 9/10 of the capacity approximatively) the liquid fully homogenized and debubbled under the effect of the centrifugal force and the polymerization causing the setting of the liquid into a solid became effective. After 10 to 15 minutes, the liquid had sufficiently solidified to prevent it from flowing out of the mould in case the rotation motion were stopped.

The gel preparation was thereafter completed by adding to the mould a second liquid comprising, for 100 ml, 7.5 ml of a 40% acrylamide solution and 1.33% of BIS-ACRYLAMIDE, 12;5 ml of TRIS 1M, pH 6.8, 79.2 ml of water and, added after degassing, 500 μl of 20% SDS, 250 μl of 10% persulfate and 75 μl of TEMED. This second portion was injected as indicated above, after the first gel was ready and the whole was allowed to further rotate 15 to 20 min, time within which the second liquid turned into a gel. This second portion constituted then the stacking gel in which, by reason of the presence during polymerization of removable pegs 24, there remained recesses in which, when the gel film is used for an electrophoretic analysis, the sample to be fractionated is injected.

Controlling the debubbling process and the progression of the centrifugation polymerization by an optical method, for instance by directing against one of the walls of the rotating mould a light signal whose direction is at a non zero angle with the latter and by measuring, either by transmission or by reflection, the modifications produced on this signal by the composition in the moulds naturally possible. Such an inspection can be carried out on a determined annular area if a fixed source is available or following a spiral shaped track if the source (and the detection means) can be moved tangentially. As the signal wave length, the UV range can be used as acrylamide gels absorb UV although methacrylate moulds are transparent to UV. Moreover, the present technique is easily suitable for manufacturing sterilized gel films in cricular disposable containers which can be thrown away after use, which limits the hazards of contamination (for instance by viral hepatitis) and enables a standardisation of the analytical methods. It is also possible to incorporate in the mould, in addition to the gellable liquid, a buffering composition which may be required for subsequent electrophoresis. Further the preparation of discontinuous gradient gels which result from step polymerization procedures and the manufacture of other special type gels can be automatically controlled by means of the optical detecting means disclosed above. Actually, when UV irradiation is used to bring about photochemical polymerization of the electrophoresis medium within the mould, the same attachments can be used (at reduced intensity) for monitoring subsequent operations, including gel formation and ultimate electrophoresis separation monitoring by means of a suitable radiation detector which collects the energy transmitted through the gel and detects the absorption (or other optical changes) due to the presence of the species being separated.

Samples of protein mixtures in isotonic saline solution (10 $\mu$l each) were injected into the gel media through slots 23 and electrodes were applied to the gel through the central and peripheral apertures in the moulds. Then electrophoresis was carried out for about 1 hr at room temperature under about 80-100V.

After the separation was completed, discs 11 and 13 were separated and development of the electropherogram was carried out by usual means to provide the characteristic pattern due to the presence of the separated proteins.

EXAMPLE 3

A 10% by weight SDS-Polyacrylamide gel was prepared according to Note 306, detasheet by LKB Produkter AB, S 16126 Bromma, Sweden. This was based on 16.5 ml phosphate buffer (0.2 mol/l; pH 7.1; 0.1% (w/v) SDS); 14.9 ml of aqueous acrylamide solution (22.8% acrylamide, 0.6% bis-acrylamide in distilled water, w/v); 1.5 ml ammonium persulfate (1.5% (w/v); distilled water); 50 $\mu$l TEMED (0.3 $\mu$g).

A circular mould such as that disclosed in FIGS. 3 and 4 was used and the gellable solution was poured therein under spinning at 3000 rpm. Curing occurred in about 2 hrs at room temperature and provided a six segment electrophoretic medium.

Three of the available six segments were used for the next steps. Samples (5 $\mu$l) of an analytical mixture to be separated were pipetted into the holes 23 in the gel after removing the pegs 24. The sample was from the "Low Molecular Weight Calibration Kit" from Pharmacia Fine Chemicals, Sweden, covering the MW range of 14.000 to 94,000 D.

The electrophoretic apparatus used was similar in shape to that disclosed in our co-pending application Ser. No. 702,721 incorporated by way of reference (see FIGS. 1 and 5 of this application). However the apparatus used in the instant Example is not rotated. It comprises a cylindrical cell of insulating material divided into two coaxial compartments (central and peripheral), by an annular partition, each containing a buffer electrolyte. The central compartment encloses an annular electrode electrically connected to a power pack. Similarly the peripheral compartment contains an annular electrode also connected to the power pack. The mould is inserted in the cylindrical apparatus cell, resting under slight pressure (provided by closing a lid of the apparatus) over the annular partition. Thus the two annular compartments are separated one from the other by a seal and the electrolytes they contain are electrically isolated except for the connection given by the electrophoretic medium contained in the sectors of the mould; this is so because one end (the axial one) of each sector channel is in contact with the electrolyte in the central compartment and the other end (the peripheral one) is in contact with the electrolyte in the other compartment.

The electrophoresis power-pack used was a LKB Multiphor 2117-301. The conditions of separation were 18-20 mA; 150V, 1 hr, room temperature.

Following electrophoresis, the gel was fixed in a trichloracetic (TCA)/sulfosalicylic acid mixture and stained with Coomassie Blue (0.25% by volume in a 10/50/40 mixture of acetic acid, n-propanol and water). Then destaining was effected with a 50/10/60 (v/v) mixture of acetic acid, methanol and water and final preservation in a water solution containing 3% (v/v) of ethanol, 1% of acetic acid and 1% of glycerol.

The separated protein fractions (MW), appearing as blue areas on the electropherogram, are listed in the Table below as a function of their distance (in mm) from the start line. This distance is also expressed as its ratio to the maximal migration distance (that corresponding to the protein with maximal mobility).

TABLE

| Protein (MW) | Distance (mm) - (ratio) | | | |
|---|---|---|---|---|
| | Segment 1 | Segment 2 | Segment 3 | Average |
| 94,000 | 19 (0.42) | 23 (0.45) | 20 (0.42) | 21 (0.43) |
| 67,000 | 23 (0.51) | 27 (0.53) | 25 (0.52) | 25 (0.52) |
| 43,000 | 28 (0.62) | 33 (0.65) | 29 (0.60) | 30 (0.62) |
| 30,000 | 34 (0.76) | 40 (0.78) | 36 (0.79) | 37 (0.76) |
| 20,100 | 41 (0.91) | 47 (0.92) | 44 (0.92) | 44 (0.92) |
| 14,400 | 45 (1.00) | 51 (1.00) | 48 (1.00) | 48 (1.00) |

This technique allows an analysis in triplicate (or more since 6 segments are available) ensuring significant accuracy and reproducibility improvements, or alternatively simultaneous analysis of several different samples.

EXAMPLE 4

A flat rectangular mould with 100 $\mu$m between the main plates of the type described in FIG. 1 and 2 was used. The bottom of the mould (cross-bar 6b) was provided in the inside with a stainless-steel electrode with a terminal on the outside of the mould. A first gellable liquid was prepared as described in Example 2 but using a 15% by weight acrylamide solution instead of a 40% one. The mould was filled at 3000 rpm to about 9/10 of its capacity with the first liquid and the latter was allowed to polymerize; after sufficient hardening (about 15-30 min. at room temperature), a stacking gel liquid was added to complete the first gel as disclosed in Example 1 and, after final curing, an analyte sample was injected at rest in the mouth of the mould. This sample was a 1 $\mu$l of aqueous solution containing 0.5 $\mu$g albumin (MW 68,000), 0.5 $\mu$g glucose oxidase (MW 160,000) and 2 $\mu$g peroxidase (MW 40,000).

An electrode was run in the front end of the gel and this electrode and that at the end of the mould were connected to a power-pack as in the previous Example. The gel was then subjected to electrophoresis under usual conditions (150V for 50 min.) after which the full mould was scanned, without staining or any further post-treatment, in a UVIKON-860 spectrophotometer (made by KONTRON, Switzerland). For this, the plate was mounted on a slidable attachment adapted in place of the usual spectrophotometer cuvette. The attachment enabled to scan the full length of the plate by 1 mm steps. The apparent absorbance was recorded at several wavelengths. The results are provided below as a function of the distance (in mm) from the base line.

| Wavelength (nm) | Absorbance at ($\lambda$) | | | | Distance (mm) |
| --- | --- | --- | --- | --- | --- |
|  | 235 | 260 | 280 | 550 |  |
| Background (approx.) | 0.03 | 0.03 | 0.01 | 0.01 | 0 |
| Peroxidase | 0.09 | 0.27 | 0.07 | 0.03 | 22 |
| Albumin | 0.05 | 0.07 | 0.03 | 0.02 | 18 |
| Glucose oxidase | 0.07 | 0.07 | 0.04 | 0.03 | 12 |

The mould used in this Example was made of polyacrylate PLEXIGLAS G5 from Röhm GmbH, Darmstadt (BDR); the walls were 2 mm thick. The absorbance measurements above result from the combined loss of light (absorbance and scattering) due to the gel layer, the protein of interest and the two plexiglass walls of the mould.

We claim:

1. A centrifugal mold for casting thin films which comprises, in combination;
   (1) a mold plate mounted on a rotational axis having an upwardly extending shoulder and an annular recess or groove around a peripheral edge of the mold plate;
   (2) a lower disc resting on said mold plate and extending from the rotational axis to the peripheral edge of the mold plate, said plate being shaped to conform to a contour of an upper face of the mold plate and terminating with an upwardly extending face in close proximity to an inner face of the shoulder on said mold plate;
   (3) an upper disc having a central opening and positioned above said lower disc said upper disc being coextensive with said lower disc, said discs being positioned so as to have a mold space therebetween;
   (4) conduit means extending from a central opening at the rotational axis of the mold to an entrance of the mold space between the upper and lower discs arranged to dispense liquid radially from the central opening to the mold space;
   (5) at least one hole near an outer end of the mold space remote from said central opening adapted to engage removable pegs; and
   (6) means for rotating said mold about said axis.

2. A centrifugal mould for casting thin films according to claim 1 which further comprises a means to form, prior to polymerization, within the space generally occupied by the liquid to be polymerized to a mass of gel, areas where the liquid cannot penetrate, said areas constituting after polymerization, placements for the introduction of samples to be analyzed into the mass of the gel.

3. A centrifugal mould for casting thin films according to claim 1 which further comprises a lower disc with an annular peripheral zone grooved to a depth equal to or exceeding the thickness of the mould space as defined by a distance between the upper and lower disc, this zone being provided to contain a first portion of gel in which one carries out a first electrophoretic separation of a sample before proceeding to a final filling of the mould to obtain a second portion of gel in contact with the first portion.

4. A centrifugal mould for casting thin films which comprises, in combination,
   (1) a lower disc having a central opening and a plurality of spaced radial recesses extending from the central opening to an outer peripheral edge of the lower disc;
   (2) an upper disc having a central opening larger than said lower disc and being in contact with said lower disc to form a plurality of mould compartments with said recesses, the compartments being defined by bottom and side walls of the recesses and portions of the upper disc which cover the recesses;
   (3) a mould plate mounted on a rotational axis supporting said lower and upper discs which is provided with an upwardly extending shoulder around its periphery which retains the upper and lower discs in position and constitutes an outer face or sidewall which limits the volume of the mould;
   (4) an annular space defined by edges of the central openings of the discs and the thickness between the discs at the recesses being held open and constituting an opening for filling the mould;
   (5) a lid means surrounding an outer perimeter of the mould which can be removably affixed to said mould plate to retain said upper and lower discs in position;
   (6) a plurality of holes in close proximity to and surrounding the central opening of said upper disc, said holes being so sized and shaped as to engage removable pegs; and
   (7) means for rotating said mould about said axis.

5. A centrifugal mould for casting thin films according to claim 4 which further comprises a circular lid which can be affixed to a plate by a fastening means and a central bolt to maintain a tight contact between the mould and said plate; the upper disc further comprising holes in which one can engage elements in the form of removable pegs whose lower parts have a section corresponding to the inside dimension of said holes and rest against an inside face of the lower disc such that they can easily be introduced therein and extracted manually therefrom.

6. A centrifugal mould for casting thin films according to claim 4 further comprising an o-ring positioned between said lid means and said upper disc in close proximity to the shoulder of said mould plate, and an o-ring in approximately the same location between the lower disc and the mould plate.

* * * * *